(12) United States Patent
Quinn et al.

(10) Patent No.: US 9,241,642 B2
(45) Date of Patent: Jan. 26, 2016

(54) SYSTEMS AND METHODS FOR MONITORING A PATIENT

(75) Inventors: David E. Quinn, Auburn, NY (US); Matthew J. Kinsley, Liverpool, NY (US)

(73) Assignee: WELCH ALLYN, INC., Skaneateles Falls, NY (US)

(\*) Notice: Subject to any disclaimer, the term of this patent is extended or adjusted under 35 U.S.C. 154(b) by 745 days.

(21) Appl. No.: 13/398,519

(22) Filed: Feb. 16, 2012

(65) Prior Publication Data

US 2013/0218033 A1 Aug. 22, 2013

(51) Int. Cl.
*A61B 5/022* (2006.01)
*A61B 5/0225* (2006.01)

(52) U.S. Cl.
CPC ............ *A61B 5/02225* (2013.01); *A61B 5/0225* (2013.01)

(58) Field of Classification Search
CPC ..................... A61B 5/022; A61B 2560/0223
See application file for complete search history.

(56) References Cited

U.S. PATENT DOCUMENTS

| | | |
|---|---|---|
| 3,699,945 A | 10/1972 | Hanafin |
| 3,765,405 A | 10/1973 | Natkanski |
| 4,178,918 A | 12/1979 | Cornwell |
| 4,331,155 A | 5/1982 | Sacks |
| 4,605,010 A | 8/1986 | McEwen |
| 4,770,175 A | 9/1988 | McEwen |
| 5,048,536 A | 9/1991 | McEwen |
| 5,089,961 A * | 2/1992 | Coble et al. .................. 600/507 |
| 5,277,187 A * | 1/1994 | Pillsbury ....................... 600/490 |
| 5,660,182 A | 8/1997 | Kuroshaki et al. |
| 5,730,139 A * | 3/1998 | Miyazaki et al. ............. 600/493 |
| 7,192,403 B2 | 3/2007 | Russell |
| 7,249,604 B1 | 7/2007 | Mohanraj |
| 7,390,303 B2 | 6/2008 | Dafni |
| 8,840,561 B2 | 9/2014 | Lane et al. |
| 2003/0233204 A1 | 12/2003 | Peel, III et al. |
| 2006/0224181 A1* | 10/2006 | McEwen et al. ............. 606/202 |
| 2007/0088224 A1* | 4/2007 | Friedman et al. ............ 600/490 |
| 2008/0262533 A1 | 10/2008 | McEwen et al. |
| 2010/0191129 A1 | 7/2010 | Williams et al. |
| 2010/0292592 A1 | 11/2010 | Parfenov et al. |
| 2011/0275944 A1* | 11/2011 | Qasem ......................... 600/493 |

FOREIGN PATENT DOCUMENTS

| | | |
|---|---|---|
| EP | 0434399 | 6/1991 |
| KR | 20080010530 A | 1/2008 |
| WO | WO2011149578 | 12/2011 |

OTHER PUBLICATIONS

Indirect Blood Pressure Finger Cuff, IP.com Prior art Database Disclosure No. IPCOM000095 dated Sep. 1, 1965, IBM, US.

(Continued)

*Primary Examiner* — Michael D'Angelo
*Assistant Examiner* — Michael Catina

(57) ABSTRACT

A system for monitoring a patient includes an inflatable cuff configured to at least partially occlude an artery of the patient, and a sensor configured to determine a first parameter associated with the at least partially occluded artery and to generate an output signal indicative of the first parameter. The system also includes a processor configured to receive the output signal and information indicative of an occlusion efficiency of the cuff. The processor is configured to determine a hemodynamic parameter of the patient based on the output signal and the information.

25 Claims, 2 Drawing Sheets

(56) References Cited

OTHER PUBLICATIONS

Bovet et al., Systematic Difference Between Blood Pressure Readings Caused by Cuff Type, Univ Lausanne Hosp. Div Hypertens, Lausanne, Switzerland, Hypertension 1994, vol. 24, No. 6 (Dec.), pp. 786-792.

Geddes et al., The error in indirect blood pressure measurement with the incorrect size of cuff, Am Heart J. Jul. 1978; 96(1); 4-8.

Amoore, Extracting oscillometric pulses from the cuff pressure: does it affect the pressures determined by oscillometric blood pressure monitors?, Blood Pressure Monitoring, vol. 11, No. 5 (Oct.), pp. 269-279.

Cuffs Independent Clinical Studies, Accessed: Nov. 1, 2011 http://www.geheathcare.com/euen/patient_monitoring/docs/Cuffs_IndependentClinicalStudies.pdf.

PCT Search Report for International application No. PCT/US2013/023592; dated Jun. 2, 2013; 11 pages.

Extended European Search Report mailed Aug. 26, 2015 for European patent application No. 13749107.2, 6 pages.

\* cited by examiner

SYSTEMS AND METHODS FOR MONITORING A PATIENT

TECHNICAL FIELD

This application is directed to systems and methods for monitoring a patient, and in particular, to systems and methods for determining a hemodynamic parameter of a patient.

BACKGROUND

Traditional non-invasive blood pressure monitoring devices operate by inflating a blood pressure cuff to a pressure above a patient's systolic blood pressure. Because the systolic pressure is usually not know prior to inflation, the cuff must be inflated to such a pressure to ensure that the patient's arterial blood flow is completely occluded. Once above systole, pressure data collected during inflation and/or deflation of the cuff is used to determine systolic and diastolic pressures of the patient.

Typically, automated non-invasive blood pressure devices have a fixed calibration to determine the pressure a cuff is applying to a limb of a patient, based on an input signal from a pressure sensor. The size, type, and/or configuration of the cuff being used, however, may introduce variation with respect to the pressure measured by the sensor versus the actual pressure a cuff is applying to a limb. Even though such variations in cuff designs or configuration may have a relatively small effect on the resulting blood pressure measurement (typically between approximately 0 mmHg and approximately 5 mmHg), such variations are large enough to cause difficulties in satisfying applicable blood pressure cuff regulations.

The systems and methods described herein are directed toward overcoming the difficulties described above.

SUMMARY

In an exemplary embodiment of the present disclosure, a system for monitoring a patient includes an inflatable cuff configured to at least partially occlude an artery of the patient, and a sensor configured to determine a first parameter associated with the at least partially occluded artery and to generate an output signal indicative of the first parameter. The system also includes a processor configured to receive the output signal and information indicative of an occlusion efficiency of the cuff. The processor is configured to determine a hemodynamic parameter of the patient based on the output signal and the information.

In a further exemplary embodiment of the present disclosure, a method of determining a hemodynamic parameter of a patient includes inflating a cuff to an occlusion pressure, wherein inflating the cuff at least partially occludes an artery of the patient. The method also includes determining a parameter associated with the at least partially occluded artery and receiving information indicative of an occlusion efficiency of the cuff. The method further includes determining the hemodynamic parameter of the patient based on the parameter and the information.

In another exemplary embodiment of the present disclosure, a method of determining a hemodynamic parameter of a patient includes determining at least one of a systolic pressure, a diastolic pressure, and a mean arterial pressure associated with an artery at least partially occluded by a cuff. The method also includes determining an occlusion efficiency of the cuff based on at least one of a size, type, and model of the cuff. The method further includes determining a hemodynamic parameter of the patient based on the at least one of the systolic pressure, the diastolic pressure, and the mean arterial pressure, and the occlusion efficiency of the cuff.

DETAILED DESCRIPTION

Figure 1:
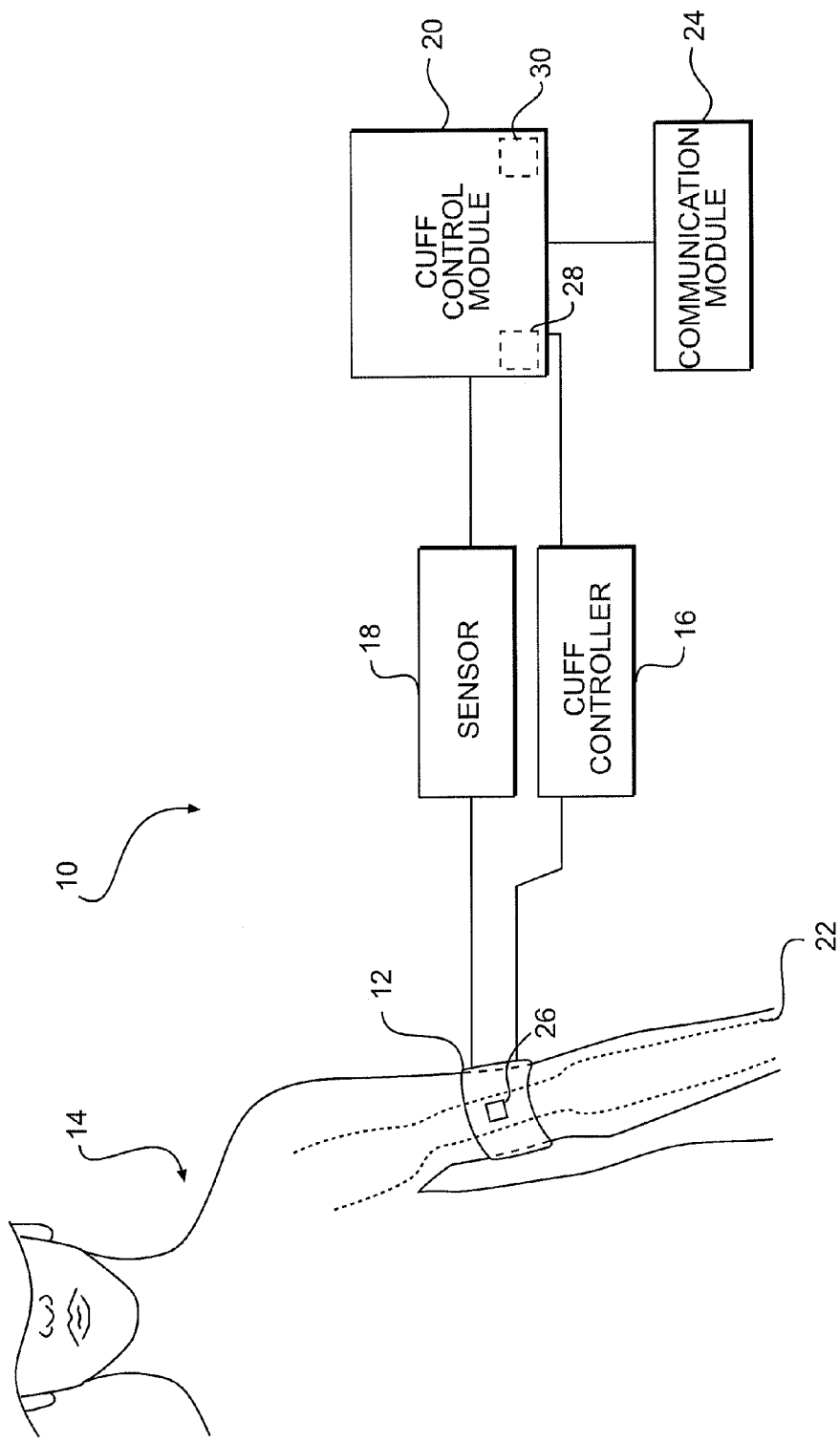
FIG. 1 illustrates a system according to an exemplary embodiment of the present disclosure.

FIG. 1 illustrates a monitoring system 10 according to an exemplary embodiment of the present disclosure. System 10 can be configured to monitor a patient 14, and in some embodiments, to determine a hemodynamic parameter of the patient 14. System 10 can include a cuff 12 configured to at least to partially occlude the movement of blood through a vessel, vein, and/or artery 22 of the patient 14. In some embodiments, cuff 12 can be configured to completely occlude an artery 22 of patient 14, and the artery 22 may be, for example, the brachial artery. For example, the cuff 12 may be inflated to any known occlusion pressure, and at such an occlusion pressure, the artery 22 may be at least partially occluded. Although shown in FIG. 1 as surrounding the upper arm of patient 14, cuff 12 may be adapted for placement on any suitable part of patient 14, including, for example, a wrist, a finger, an upper thigh, or an ankle. In addition, one or more cuffs 12 could be placed at different locations about and/or on patient 14 for use with system 10.

The exemplary cuffs 12 of the present disclosure may be formed from any medically approved material known in the art. Such materials may be highly flexible, durable, and suitable for contact with, for example, the skin of the patient 14. Such materials may also be tear-resistant, fluid-impermeable, and recyclable. Such materials may include, for example, paper, cloth, mesh and/or polymers such as polypropylene or polyethylene. In still further exemplary embodiments, such materials may be coated and/or otherwise treated with one or more additives that cause the material to become biodegradable within a desired time interval (e.g., within 2 to 3 months). Each of the exemplary cuffs 12 described herein may have a respective length, width, and inflated height suitable for use with a particular patient 14. For example, a first cuff 12 intended to be used with an adolescent patient 14 may have a first deflated length and a first deflated width, and a second cuff 12 intended for use with an adult patient 14 may have a corresponding second deflated length and second deflated width. In such an exemplary embodiment, the first deflated length may be less than the second deflated length and the first deflated width may be less than the second deflated width. Unless otherwise indicated, the lengths and widths referred to for the duration of this disclosure are intended to be deflated lengths and widths. In exemplary embodiments, inflated lengths and widths of the exemplary cuffs described herein may be different than the corresponding deflated lengths and widths.

The cuff 12 may include one or more bladders (not shown) or other like inflatable devices. Such a bladder may be formed from a single piece of material or, alternatively, from two or more pieces of material that are joined together through heat sealing, ultrasonic or RF welding, adhering, and/or other like processes. In still further exemplary embodiments, the cuff 12 may form one or more inflatable pockets that perform the same functions as a bladder. In such exemplary embodiments, the bladder may be omitted. It is understood that the cuff 12 and/or bladder may be inflatable to an occlusion pressure of approximately 160 mm Hg or greater to assist in at least partially occluding the artery 22. In exemplary embodiments, the cuff 12 may include one or more ports (not shown) fluidly connected to the internal pocket or bladder to assist with inflation and/or deflation thereof.

The pressure or volume of fluid within cuff 12 may be controlled by a cuff controller 16 operably associated with the cuff 12. Cuff controller 16 can include a pump or similar device to inflate and/or deflate the cuff 12. For example, cuff controller 16 could supply cuff 12 with a fluid such as air to increase the pressure or volume within the cuff 12. In other embodiments, cuff controller 16 could include mechanical, electrical, or chemical devices configured to control occlusion of the artery 22 via cuff 12. The cuff controller 16 may be mechanically, fluidly, and/or operably connectable to one or more of the ports described herein to assist in inflating and/or deflating the cuff 12.

In some embodiments, cuff controller 16 can generally maintain cuff 12 at about a target or reference pressure. For example, once a target or reference pressure has been chosen, cuff controller 16 could inflate and maintain the cuff 12 to the target or reference pressure. While the present disclosure refers to a target or reference pressure, it should be understood that the actual pressure applied by cuff 12 may vary slightly from the target or reference. For example, the actual pressure applied to patient 14 may generally remain within appropriate limits, such as, for example, within 2%, 5%, 10%, or 20% of the target or reference pressure. This difference between the chosen target or reference pressure and the actual pressure applied by the cuff 12 may be caused by the occlusion efficiency of the respective cuff 12. A cuff's "occlusion efficiency" may be defined as the ease or difficulty with which air pressure within the cuff 12 is transferred to force on the underlying artery 22. For example, cuffs 12 having a higher occlusion efficiency may be capable of applying a relatively greater force to such an artery 22 at a given inflation pressure than a like cuff 12 having a relatively lower occlusion efficiency. Prior to use, automated non-invasive blood pressure monitoring devices are typically calibrated based on a standard occlusion efficiency associated with the cuff type to be used for blood pressure measurement. While such calibration is effective when the appropriate cuff type is used with the monitoring device, such calibration is problematic when clinicians or other health care professionals use cuffs of a different type or design, and thus having different occlusion efficiencies, with the blood pressure monitoring device. Such calibration can also be problematic when the proper cuff-type is used if the cuff has a different occlusion efficiency than that used to calibrate the monitoring device.

System 10 can further include a sensor 18 configured to receive a signal associated with the patient 14. In each of the exemplary embodiments described herein, the sensor 18 may determine one or more parameters associated with an at least partially occluded artery 22 of the patient 14. Such parameters may include, for example, a systolic pressure, a diastolic pressure, a mean arterial pressure, and/or other known parameters associated with the cuff 12, the artery 22, and/or the patient 14. As will be described in greater detail below, in further exemplary embodiments the sensor 18 may be configured to determine one or more of an oscillation signal strength, an ambient temperature, a humidity, a cumulative cycle count of the cuff 12, a volume of the cuff 12, an occlusion pressure of the cuff 12, a cumulative time associated with the cuff 12 being inflated to a reference volume and/or pressure, and/or other like parameters. In exemplary embodiments, the reference pressure may be approximately 100 mm Hg, and the target pressure may be equal to the reference pressure. The reference volume may be any volume of the cuff 12 and/or the bladder associated with reaching such a reference pressure. The sensor 18 may comprise devices including, but not limited to, one or more of a pressure sensor, a thermometer, a thermocouple, a hygrometer, and/or a timer. The sensor 18 may be located at positions including, but not limited to, within, on, or about cuff 12. System 10 may further include a plurality of sensors 18, and may include a high-resolution sensor or pneumatic sensor designed to operate in conjunction with cuff 12.

In some embodiments, the sensor 18 can be configured to receive a signal associated with an at least partially occluded artery 22 of patient 14. Such an input signal can arise from blood movement through a partially occluded artery 22 or from a signal associated with an occluded blood vessel. Sensor 18 could sample various aspects or characteristics of the artery 22 multiple times at various intervals. In additional exemplary embodiments, sensor 18 could provide an indication of blood vessel movement, such as, for example, oscillations arising from vascular expansion or contraction. Such oscillations may produce a signal that is detected by the sensor 18, and the strength of such an oscillation signal may be used to determine a hemodynamic parameter of the patient 14. For example, sensor 18 could be configured to detect an occlusion pressure or volume of cuff 12 that may vary periodically with the cyclic expansion and contraction of the artery 22 of patient 14.

In additional exemplary embodiments, the sensor 18 may be configured to read, scan, sense, detect, and/or otherwise input information associated with the cuff 12. Such information may include, for example, an occlusion efficiency that is particular to the actual cuff 12 being used, or an occlusion efficiency associated with the type, size, design, model, and/or style of cuff 12 being used. It is understood that the type, size, design, model, and/or style of the cuff 12 may be parameters that are unique or particular to the actual cuff 12 being used. For example, such parameters may include and/or may be indicative of the length, width, inflated height, and/or other dimensions of the cuff 12, the shape of the cuff 12, the number of bladders included in the cuff 12, the length, width, and/or inflated height of such bladders, the maximum inflated volume of the cuff 12, materials used to construct the cuff 12, and whether the cuff 12 is intended for use with a child, adolescent, adult, elderly, and/or bariatric patient 14, among other things. In such exemplary embodiments, the sensor 18 may comprise an RFID reader, a barcode reader, an MICR reader, a conductance sensor, a resistance sensor, a magnetic sensor, and/or any other like reading device known in the art. Such a sensor 18 may be configured to sense, scan, detect, and/or otherwise read information carried by one or more information features 26 associated with the cuff 12. In addition to standard text, such information features 26 may comprise one of an RFID tag, a barcode, MICR printing, a conductive, resistive, and/or magnetic strip of material, and/or other known means for providing information. For example, such information features 26 may communicate an occlusion efficiency of the cuff 12 to the sensor 18 and/or to a user of the system 10. Such information features 26 may also communicate an identification parameter particular to the cuff 12. Such an identification parameter may be indicative of, for example, the type, size, design, model, and/or style of the cuff 12 being used. Such an identification parameter may also comprise, for example, a serial number, a model number, a part number, and/or any other like information enabling the particular cuff 12 to be identified for purposes of tracking or recording, for example, a cumulative cycle count, an age of the cuff, and/or any of the other parameters described herein.

One or more such information features 26 may be disposed on an outer exposed surface of the cuff 12 for reading by the sensor 18 or, alternatively, may be embedded within and/or formed integrally with the cuff 12. The sensor 18 may further comprise one or more cameras, scopes, optical devices, and/or other like components configured to read information from the information feature 26. In such exemplary embodiments, the sensor 18 and/or components of the system 10 in communication with the sensor 18 may employ various pattern recognition software, identification software, and/or other like control hardware/software to assist in reading the information provided by the information feature 26. In such embodiments, the information feature 26 may include text, characters, numerals, figures, and/or other indicia that is screen printed, encoded, and/or otherwise viewable on a surface thereof. Alternatively, such indicia may be printed, encoded, and/or otherwise disposed on a viewable surface of the cuff 12. Sensor 18 can further be configured to generate one or more output signals indicative of each respective parameter that is determined. The output signal may be generated based on an input signal received from patient 14. In one aspect, the output signal can include a representation of an input signal associated with cuff 12 and/or patient 14.

One or more of the parameters determined by the sensor 18 may be used to determine one or more hemodynamic parameters of the patient 14. As described herein, a hemodynamic parameter can include any indication of cardiac or vascular health, such as, for example, an indication of cardiac, circulatory, or vascular functionality. Specifically, a hemodynamic parameter can include a heart rate, a blood pressure, a vessel compliance, an aortic index, an augmentation index, a reflected wave ratio, and/or an indication of treatment. Such a blood pressure can include systolic pressure, diastolic pressure, and/or mean arterial pressure, and vessel compliance may include, for example, arterial stiffness. An indication of treatment can include a parameter reflecting the effect of a drug treatment, or one or more treatments of a disease state.

In some embodiments, a hemodynamic parameter can be determined based on a suprasystolic measurement. In other embodiments, a hemodynamic parameter can be determined based on a first set of data obtained during inflation of cuff 12 and a second set of data obtained during general maintenance of cuff 12 at about a target or reference pressure. Such a target or reference pressure may be, for example, an occlusion pressure wherein the artery 22 is at least partially occluded. The first or second sets of data can include various data associated with a signal waveform associated with patient 14 and/or cuff 12, and may include oscillation signal strength, amplitude, frequency, morphology, feature, or mathematically derived data. Data may be derived from a derivative, integration, or frequency analysis, such as, for example, a fast-Fourier transform. Data may also be derived from various algorithms, including curve fitting, a neural network, filtering, smoothing, or data processing. It is understood that the system 10 may comprise any known oscillometric or auscultation system, and that the system 10 may be configured to perform and/or otherwise employ any known oscillometric or auscultation methods.

Cuff 12, cuff controller 16, and sensor 18 may be operably associated with a cuff control module 20. Specifically, cuff control module 20 could include one or more processors 28 configured to control one or more operations of cuff 12, cuff controller 16, and/or sensor 18. For example, cuff control module 20 can control inflation and/or deflation of cuff 12 via control of cuff controller 16. The cuff control module 20 and/or one or more of the processors 28 associated therewith may be configured to, for example, receive the output signals generated by the sensor 18. The cuff control module 20 and/or the one or more processors 28 may also be configured to receive information, from the sensor 18 and/or from an operator of the system 10, indicative of the occlusion efficiency of the cuff. In an exemplary embodiment, such information may be sent to the cuff control module 20 by the sensor 18 as one or more of the output signals described above. The cuff control module 20 and/or the one or more processors 28 may be configured to determine a hemodynamic parameter of the patient 14 based on, for example, an output signal of the sensor 18 and/or the information indicative of occlusion efficiency.

In some embodiments, cuff control module 20 can calculate a target pressure. This calculation may be based on an output signal from sensor 18, as described above. Cuff control module 20 may also control inflation of cuff 12, inflation of cuff 12 to the target pressure, or generally maintaining inflation of cuff 12 at about the target pressure. For example, the cuff control module 20 could calculate a target pressure during inflation of cuff 12. Such a calculation could take less than about 15 seconds. Cuff control module 20 could then generally maintain cuff 12 at about the target pressure for a defined time period, such as, for example, less than about 10 seconds. In other embodiments, the target pressure could be generally maintained for a defined number of cardiac cycles, such as, for example, six, eight, or ten cycles. Such cardiac cycle data may be available upon reaching the target pressure.

In an exemplary embodiment, the cuff control module 20 and/or the one or more processors 28 thereof may include a signal analysis module 30 configured to analyze one or more signals received from the sensor 18 and/or other inputs. For example, the signal analysis module 30 can include one or more filters configured to filter a signal associated with sensor 18 or cuff control module 20. Such filters can include band-pass, high-pass, or low-pass filters. In such exemplary embodiments, the signal analysis module 30 may assist in determining the hemodynamic parameter of the patient 14.

As shown in FIG. 1, the system 10 can further include a communication module 24 configured to provide communication to patient 14 or one or more operators. For example, communication module 24 could include a display configured to display one or more hemodynamic parameters. In other embodiments, communication module 24 could include a wireless or other known transmitter configured to transmit data to a remote location. Communication module 24 may further include audio output to communicate with patient 14 and/or an operator of system 10.

In addition to the components outlined above, system 10 may include various other components as required, such as, for example, a memory, a power source, and a user input device. One or more components described herein may be combined or may be separate and operate with wireless or wired communication links. Moreover, the various components of system 10 could be integrated into a single processing unit or may operate as separate processors 28. For example, the cuff control module 20, processor 28, sensor 18, communication module 24, and/or signal analysis module 30 described herein may be disposed within a single housing, and such a housing may be configured for handheld use. In operation, one or more processors 28 can be configured to operate in conjunction with one or more software programs to provide the functionality of system 10.

Figure 2:
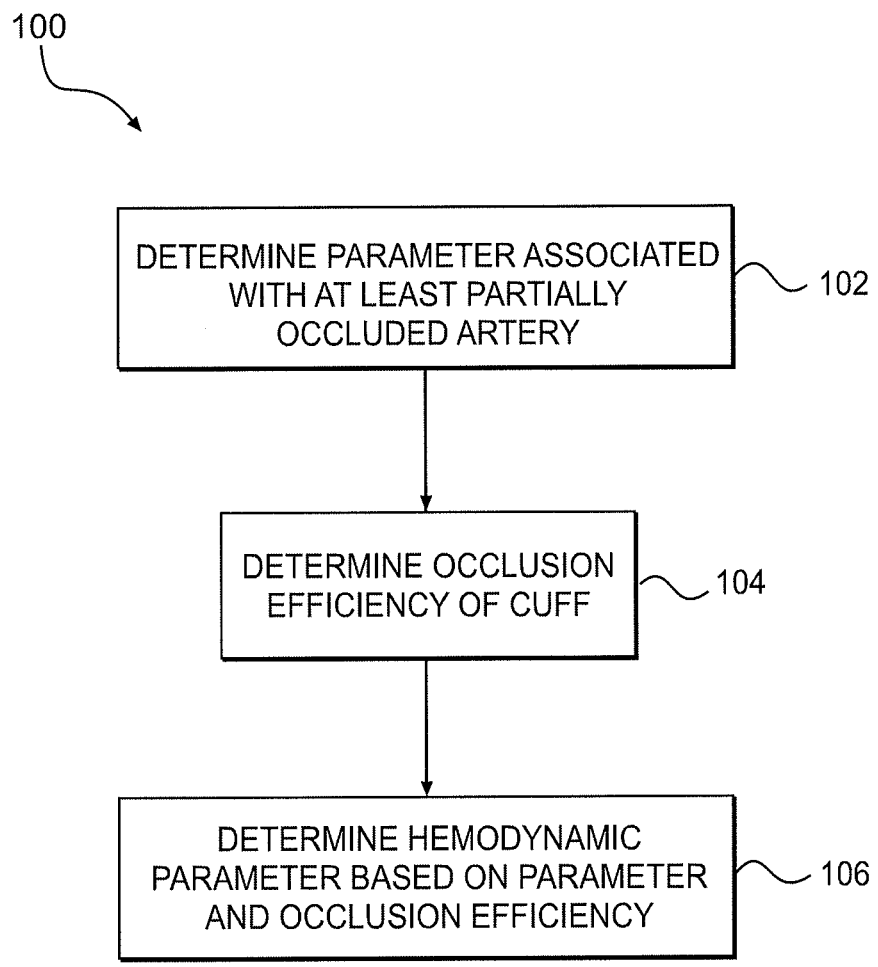
FIG. 2 shows a flow chart illustrating an exemplary method of the present disclosure.

As shown in the exemplary flow chart 100 illustrated in FIG. 2, methods of monitoring the patient 14 and/or determining a hemodynamic parameter of the patient 14 may include determining one or more parameters associated with the artery 22 as well as an occlusion efficiency of the cuff 12 being used. Such method may comprise oscillometric methods, auscultation methods, and/or any other patient monitoring methods. For example, such methods may include determining a parameter of the patient (Step: 102). Such a parameter may include, for example, at least one of a systolic pressure, a diastolic pressure, and a mean arterial pressure associated with the artery 22 while the artery 22 is at least partially occluded by the cuff 12. Such methods may also include determining an occlusion efficiency of the cuff (Step: 104), and such an occlusion efficiency may be particular to the cuff 12 being used. For instance, such an occlusion efficiency may be based on at least one of the size, type, and model of the cuff 12. Such methods may further include determining a hemodynamic parameter of the patient 14 based on the parameter and the occlusion efficiency (Step: 106). It is understood that the various method steps described herein, and illustrated in exemplary FIG. 2, may be performed in any desirable order. The various aspects of such exemplary methods will be described in greater detail below.

In exemplary methods of using the monitoring system 10, the occlusion efficiency associated with the cuff 12 may be determined in any number of ways. For example, the occlusion efficiency may be determined through clinical testing in which a number of blood pressure measurements or other like measurements are taken using the cuff 12 and the sensor 18. These measurements may then be compared to corresponding measurements taken using a reference cuff of the same type, size, design, model, and/or style, but known to have a near perfect occlusion efficiency. The occlusion efficiency of such a reference cuff may have a negligible effect on the blood pressure measurements taken with the reference cuff. In such an exemplary embodiment, the occlusion efficiency of the cuff 12 may be based on a difference between a pressure applied by the reference cuff when the reference cuff is inflated to a target or reference pressure, and a pressure applied by the cuff 12 to, for example, an at least partially occluded artery 22, when the cuff 12 is inflated to the same target or reference pressure. Such a difference may result in a measurement offset that is particular to the cuff 12. This offset may be recorded and/or otherwise permanently associated with the cuff 12, and this unique offset may be used as a correction factor by the system 10 when the cuff 12 is used for future measurements.

In other exemplary embodiments, the occlusion efficiency of the cuff 12 may be determined through a series of bench tests using the cuff 12 and a pressure testing apparatus. Such an apparatus may include, for example, a structure shaped like a limb of a patient 14 and equipped with one or more sensors configured to detect the pressure applied to the limb-shaped structure. In such exemplary embodiments, the cuff 12 may be disposed about the structure, and may be inflated to a target or reference pressure. The sensors associated with the limb-shaped structure may determine the actual pressure applied by the cuff 12, and this actual pressure may be compared to the reference pressure. A difference between these two pressures may result in a measurement offset that is particular to the cuff 12. As described above, this offset may be recorded and/or otherwise permanently associated with the cuff 12, and this unique offset may be used as a correction factor by the system 10 when the cuff 12 is used for future measurements. Such offsets may be one way of quantifying the occlusion efficiency used in determining a hemodynamic parameter of the patient 14. In other exemplary embodiments, these or other performance metrics associated with the cuff 12 may be used to quantify the occlusion efficiency. For example, percentages, functions, and/or other like metrics may also be used to quantify the occlusion efficiency offsets described herein.

In exemplary embodiments, the unique occlusion efficiency of the cuff 12 may be used to modify and/or otherwise correct a hemodynamic parameter determination made using the system 10. In such embodiments, the occlusion efficiency may be combined with any of the parameters described above to affect such a determination. It is understood that such a combination may be performed through the use of one or more equations, algorithms, control functions, and/or other means. In such exemplary embodiments, the cuff 12 may be inflated to an occlusion pressure, and inflating the cuff 12 to the occlusion pressure may at least partially occlude an artery 22 of the patient 14. The sensor 18 may then determine one or more parameters associated with the at least partially occluded artery 22. An output signal indicative of the one or more parameters may then be sent by the sensor 18 to the cuff control module 20 for use in determining the hemodynamic parameter. The cuff control module 20 may also receive information indicative of the occlusion efficiency of the cuff 12. Such information may be received from the sensor 18 in the form of an additional output signal. Alternatively, such information may be received from a user entering such information into the cuff control module 20 via one or more operator input devices. In still another exemplary embodiment, the unique occlusion efficiency of the cuff 12 may be stored within a memory of the cuff control module 20. Such a stored occlusion efficiency may be retrieved from memory by the cuff control module 20 in response to receiving, for example, information including and/or based on an identification parameter particular to the cuff 12. Such a stored occlusion efficiency may also be retrieved from the memory based on information including the type, size, design, model, and/or style of the cuff 12 being used. In further exemplary embodiments, the cuff control module 20 may prohibit use of the system 10 if the occlusion efficiency of the cuff 12 cannot be retrieved, is not entered properly, and/or is otherwise unknown. For example, the cuff control module 20 may prohibit a hemodynamic parameter determination or operation, such as by disabling the cuff controller 16, the sensor 18, and/or the cuff 12, in response to a failure to enter the occlusion efficiency or an incorrect occlusion efficiency entry.

Once the occlusion efficiency has been retrieved or properly entered by the user, one or more algorithms may utilize the occlusion efficiency particular to the cuff 12 in determining a blood pressure or other hemodynamic parameter of the patient 14. In additional exemplary embodiments, one or more algorithms may utilize the occlusion efficiency in combination with one or more empirically derived variables in determining the hemodynamic parameter. In such exemplary embodiments, the variable may be, for example, a scaling factor derived based on test data and/or other information associated with the cuff 12 or based on predefined ranges of other parameters such as, for example, systolic and diastolic estimates or the time to inflate the cuff 12. Such a variable may, for example, be derived based on the occlusion efficiency of the cuff 12. In such exemplary embodiments, the variable may scale and/or otherwise affect the hemodynamic parameter determination based on the occlusion efficiency of the cuff 12. For example, when using a first cuff known to be less efficient than a like second cuff, the system 10 may calculate the hemodynamic parameter using the occlusion efficiency in combination with a relatively large variable. Such a relatively large variable may result in a correspondingly large adjustment in the determined hemodynamic parameter.

In still further exemplary embodiments, information received by the cuff control module 20 from the sensor 18 and/or from the operator may be indicative of the occlusion efficiency of the cuff 12 as well as one or more additional parameters. For example, the information received by the cuff control module 20 may be based on the occlusion efficiency and at least one of the empirically derived variable, a cumulative time associated with inflating the cuff 12 to a reference volume, a volume of the cuff 12 at the occlusion pressure, a surface area of contact between the cuff 12 at the occlusion pressure and the patient 14, and a value indicative of the size of the cuff 12. For example, a unique numeric value may be associated with each cuff 12 depending on the shape, volume, dimensions, and/or other characteristics thereof.

In further exemplary embodiments, the information received by the cuff control module 20 may be based on the occlusion efficiency, an empirically derived variable, and at least one of a numeric value indicative of the tone, muscularity, fat content, and/or other characteristics of an arm of the patient 14, a strength of a pulse or other oscillation signal sensed by the sensor 18 during occlusion of the artery 22, an ambient temperature of the environment in which the cuff 12 is used, a humidity of the environment in which the cuff 12 is used, a cumulative use and/or cycle count of the cuff 12, a metric and/or other numeric value associated with an arterial stiffness of the patient 14, an age of the patient 14, a deflated surface area of a bladder associated with the cuff 12, and an age of the cuff 12. In such exemplary embodiments, the occlusion efficiency specific and/or particular to the respective cuff 12 being used may be combined with any of the parameters described above to affect a hemodynamic parameter determination. Such parameters may also generally be referred to as, for example, "first parameters," "arterial parameters," "cuff parameters," and/or "patient parameters." As described above, such a combination may be performed through the use of one or more equations, algorithms, control functions, and/or other means utilizing these parameters as inputs. In such exemplary embodiments, the empirically derived variable may be used as a scaling factor to increase the accuracy of the hemodynamic parameter determination.

It is understood that by using the occlusion efficiency of the cuff 12, as well as the other information, parameters, and/or variables discussed above, in determining a hemodynamic parameter of a patient 14, the accuracy of such determinations may be improved. For example, the methods described herein may reduce the error associated with such hemodynamic parameter determinations such that applicable medical device regulations may be satisfied. As known systems are not configured to utilize an occlusion efficiency that is unique to the cuff in determining a hemodynamic parameter of a patient, the systems and methods described herein are more accurate and more reliable than existing systems.

Other embodiments of the present disclosure will be apparent to those skilled in the art from consideration of the specification and practice of the disclosure contained herein. For example, in additional exemplary embodiments, the system 10 may comprise any known automated or manual auscultation system. In such exemplary embodiments, the system 10 may further include one or more microphones or other like sound sensors configured to sense and/or otherwise detect auscultation signals associated with the artery 22. Accordingly, the methods described herein may be employed by either an oscillometric system or an auscultation system. It is intended that the specification and examples be considered as exemplary only, with a true scope and spirit of the present disclosure being indicated by the following claims.

What is claimed is:

1. A system for monitoring a patient, comprising:
   an inflatable cuff configured to at least partially occlude an artery of the patient;
   a sensor configured to determine a first parameter associated with the at least partially occluded artery and to generate an output signal indicative of the first parameter; and
   a processor configured to receive the output signal and information indicative of an occlusion efficiency of the cuff, and to determine a hemodynamic parameter of the patient based on the output signal and the occlusion efficiency, wherein the occlusion efficiency is used as an input value in calculating the hemodynamic parameter.

2. The system of claim 1, wherein the first parameter comprises one of a systolic pressure, a diastolic pressure, and a mean arterial pressure.

3. The system of claim 1, wherein the hemodynamic parameter comprises one of a heart rate, a blood pressure, and an arterial stiffness.

4. The system of claim 1, wherein the sensor comprises a pressure sensor.

5. The system of claim 1, wherein the occlusion efficiency is based on a difference between a pressure applied by a reference cuff when the reference cuff is inflated to a reference pressure, and a pressure applied by the cuff when the cuff is inflated to the reference pressure.

6. The system of claim 1, wherein the sensor and the processor are disposed within a single housing.

7. The system of claim 1, wherein the cuff further comprises an information feature communicating the occlusion efficiency of the cuff.

8. A method of determining a hemodynamic parameter of a patient, comprising:
   inflating, with a control module, a cuff to an occlusion pressure, the cuff having an occlusion efficiency particular to the cuff, wherein inflating the cuff at least partially occludes an artery of the patient;
   determining, with a sensor associated with the control module, a parameter associated with the at least partially occluded artery;
   receiving, with the control module, information indicative of the occlusion efficiency of the cuff; and
   determining, with the control module, the hemodynamic parameter of the patient based on the parameter and the occlusion efficiency, wherein the occlusion efficiency is used by the control module as an input value in calculating the hemodynamic parameter.

9. The method of claim 8, wherein the hemodynamic parameter is determined based on the occlusion efficiency of the cuff, the parameter, and an empirically derived variable, and wherein the variable is derived based on the occlusion efficiency of the cuff.

10. The method of claim 8, wherein the received information is based on the occlusion efficiency and a cumulative time associated with the cuff being inflated to a reference pressure.

11. The method of claim 8, wherein the received information is based on the occlusion efficiency and a surface area of contact between the cuff at the occlusion pressure and the patient.

12. The method of claim 8, wherein the received information is based on the occlusion efficiency and a value indicative of a cuff size.

13. The method of claim 8, wherein the received information is based on the occlusion efficiency and a value indicative of at least one of an arm tone of the patient, an oscillation signal strength, an ambient temperature, a humidity, a cumulative cycle count of the cuff, an arterial stiffness of the patient, an age of the patient, a deflated surface area of a bladder associated with the cuff, a cuff size, and an age of the cuff.

14. The method of claim 8, wherein the hemodynamic parameter comprises one of a heart rate, a blood pressure, and an arterial stiffness.

15. The method of claim 8, wherein the occlusion efficiency is based on a difference between a pressure applied by a reference cuff when the reference cuff is inflated to a reference pressure, and a pressure applied to the at least partially occluded artery by the cuff when the cuff is inflated to the reference pressure.

16. The method of claim 8, wherein the information is based on an identification parameter particular to the cuff.

17. A method of determining a hemodynamic parameter of a patient, comprising:
  determining, with a sensor, at least one of a systolic pressure, a diastolic pressure, and a mean arterial pressure associated with an artery at least partially occluded by a cuff, the cuff having an occlusion efficiency particular to the cuff;
  determining the occlusion efficiency of the cuff based on at least one of a size, type, and model of the cuff; and
  determining, with a control module associated with the sensor and the cuff, a hemodynamic parameter of the patient based on the at least one of the systolic pressure, the diastolic pressure, and the mean arterial pressure, and the occlusion efficiency of the cuff, wherein the occlusion efficiency is used by the control module as an input value in calculating the hemodynamic parameter.

18. The method of claim 17, further including receiving an input indicative of the occlusion efficiency.

19. The method of claim 17, wherein the hemodynamic parameter is calculated based on an empirically derived variable, and wherein the variable is derived based on the occlusion efficiency of the cuff.

20. The method of claim 17, wherein the hemodynamic parameter is calculated based on a value indicative of at least one of an arm tone of the patient, an oscillation signal strength, an ambient temperature, a humidity, a cumulative cycle count of the cuff, an arterial stiffness of the patient, an age of the patient, a deflated surface area of a bladder associated with the cuff, a cuff size, and an age of the cuff.

21. The method of claim 17, wherein the hemodynamic parameter is blood pressure.

22. The method of claim 17, wherein the hemodynamic parameter is arterial stiffness.

23. The method of claim 17, wherein the occlusion efficiency is based on a difference between a pressure applied by a reference cuff when the reference cuff is inflated to a reference pressure, and a pressure applied by the cuff when the cuff is inflated to the reference pressure.

24. The method of claim 8, further comprising displaying one or more of the hemodynamic parameter, the occlusion efficiency, and the parameter via a communication module operably connected to the control module, the control module operable to control display of the one or more of the hemodynamic parameter, the occlusion efficiency, and the parameter on the communication module.

25. The method of claim 8, wherein operation of at least one of the sensor and the cuff is permitted by the control module based at least in part on the occlusion efficiency.

\* \* \* \* \*